US006770729B2

(12) United States Patent
Van Antwerp

(10) Patent No.: US 6,770,729 B2
(45) Date of Patent: Aug. 3, 2004

(54) POLYMER COMPOSITIONS CONTAINING BIOACTIVE AGENTS AND METHODS FOR THEIR USE

(75) Inventor: William P. Van Antwerp, Valencia, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 59 days.

(21) Appl. No.: 10/260,786

(22) Filed: Sep. 30, 2002

(65) Prior Publication Data

US 2003/0031699 A1 Feb. 13, 2003

(51) Int. Cl.$^7$ .............................................. C08G 18/52
(52) U.S. Cl. ...................... 528/77; 424/422; 424/423; 424/424; 424/425; 427/2.12; 427/58; 428/423.1; 528/85
(58) Field of Search ...................... 428/423.1; 427/2.12, 427/58; 528/77, 85; 424/422, 423, 424, 425

(56) References Cited

U.S. PATENT DOCUMENTS

| | | |
|---|---|---|
| 4,484,987 A | 11/1984 | Gough |
| 4,759,828 A | 7/1988 | Young et al. |
| 4,816,130 A | 3/1989 | Karakelle et al. |
| 4,890,620 A | 1/1990 | Gough |
| 4,909,908 A | 3/1990 | Ross et al. |
| 4,990,357 A * | 2/1991 | Karakelle et al. ........... 427/2.12 |
| 5,000,955 A | 3/1991 | Gould et al. |
| 5,108,819 A | 4/1992 | Heller et al. |
| 5,128,408 A | 7/1992 | Tanaka et al. |
| 5,165,407 A | 11/1992 | Wilson et al. |
| 5,214,119 A | 5/1993 | Leir et al. |
| 5,238,732 A | 8/1993 | Krishnan |
| 5,239,036 A | 8/1993 | Krishnan |
| 5,239,037 A | 8/1993 | Krishnan |
| 5,322,063 A | 6/1994 | Allen et al. |
| 5,334,691 A | 8/1994 | Gould et al. |
| 5,390,671 A | 2/1995 | Lord et al. |
| 5,391,250 A | 2/1995 | Cheney, II et al. |
| 5,484,818 A | 1/1996 | De Vos et al. |
| 5,614,586 A | 3/1997 | Tang et al. |
| 5,674,275 A | 10/1997 | Tang et al. |
| 5,777,060 A | 7/1998 | Van Antwerp |
| 5,786,439 A | 7/1998 | Antwerp et al. |
| 6,017,577 A * | 1/2000 | Hostettler et al. .......... 427/2.12 |
| 6,020,071 A * | 2/2000 | Watson ..................... 428/423.1 |
| 6,068,853 A | 5/2000 | Giannos et al. |
| 6,200,599 B1 | 3/2001 | Nantz et al. |
| 6,231,600 B1 | 5/2001 | Zhong |
| 6,273,913 B1 | 8/2001 | Wright et al. |
| 6,287,285 B1 | 9/2001 | Michal et al. |
| 6,287,588 B1 | 9/2001 | Shih et al. |
| 6,300,458 B1 | 10/2001 | Vandenberg |
| 6,306,422 B1 | 10/2001 | Batich et al. |
| 6,322,815 B1 | 11/2001 | Saltzman et al. |
| 6,358,556 B1 | 3/2002 | Ding et al. |

FOREIGN PATENT DOCUMENTS

| | | |
|---|---|---|
| EP | 0 192 237 | 8/1986 |
| EP | 0 390 390 | 10/1990 |
| EP | 0 483 941 | 5/1992 |
| EP | 0 535 898 | 4/1993 |
| EP | 0 624 612 A1 | 11/1994 |
| GB | 2194843 | 3/1988 |
| GB | 2235462 | 3/1991 |
| WO | WO 92/21976 | 12/1992 |
| WO | WO 95/15352 | 6/1995 |
| WO | WO 96/15443 | 5/1996 |
| WO | WO 96/30431 | 10/1996 |

OTHER PUBLICATIONS

Ash, "Imdustrial Chemical Thesaurus," vol. 1: Chemical to Tradename Reference, 1992 ed., 452–453.

Berk et al., "Pharmacologic Roles of Heparin and Glucocorticoids to Prevent Restenois After Coronary Angiosplasty," J. Am. Coll. Cardiol., 1991, 17: 111B–117B.

Clowes et al., "Kinetics of Cellular Proliferation After Arterial Injury. II. Inhibition of Smooth Muscle Growth by Heparin," Lab. Invest., 1985, 52(6):611–616.

Clowes et al., "Kinetics of Cellular Proliferation After Aterial Injury. IV. Heparin Inhibits Rat Smooth Muscle Mitogenesis and Migration," Circ. Res., 1986, 58: 839–845.

Clowes et al., "Suppression by Heparin of Smooth Muscle Cell Proliferation in Injured Arteries," Nature, 1977, 265: 625–626.

Colburn et al., "Dose Responsive Suppression of Myointimal Hyperplasia by Dexamethasone," J. Vasc. Surg., 1992, 15: 510–518.

Crescenzi et al., "Aqueous Solution Properties of Bacterial Poly–γ–D–Glutamate," Polymer Preprints, 1994, 407–408.

Currier et al., "Colchicine Inhibits Restenosis After Iliac Angioplasty in the Atherosclerotic Rabbit," Circulation, 1989, 80(4): II –66.

Dang et al., "Dextran Retention in the Rat Brian Following Release from a Polymer Implant," Biotech. Progress, 1992, 8:527–532.

Ferns et al., "Inhibition of Neointimal Smooth Muscle Accumlation After Angioplasty by an Antibody to PDGF," Science, 1991, 253: 1129–1132.

Gregory et al., "Rapamycin Inhibits Arterial Intimal Thickening Caused by Both Alloimmune and Mechanical Injury," Transplantation, 1993, 55: 1409–1418.

Guyton et al., "Inhibition of Rat Arterial Smooth Muscle Cell Proliferation by Heparin," Circ. Res., 1980, 46:625–634.

(List continued on next page.)

Primary Examiner—John M. Cooney, Jr.
(74) Attorney, Agent, or Firm—Gates & Cooper LLP

(57) ABSTRACT

Embodiments of the invention provide polymer coated implantable medical devices having a bioactive material posited in or on at least a portion of the coating layer, wherein the coating layer provides for the controlled release of the bioactive material from the coating layer. Preferably, the medical device is an intravascular stent.

18 Claims, 1 Drawing Sheet

OTHER PUBLICATIONS

Hansson et al., "Interferon–γ Inhibits Arterial Stenosis After Injury," Circulation, 1991, 84: 1266–1272.

Hofma et al., "Recent Developments in Coated Stents," Curr Interv Cardiol Rep, 2001, 3(1):28–36.

Hohjoh, "RNA Interferance(RNAi) Induction with Various Types of Synthetic Oligonucleotide Duplexes in Cultured Human Cells," FEBS Lett, 2002, 521(1–3): 195–199.

Kipshidze et al., "Intramural Coronary Delivery of Advanced Antisense Oligonucleotides Reduces Neointimal Formation in the Porcine Stent Restenosis Model," J. Am. Coll. Cardiol., 2002, 39(10): 1686–1691.

Kou et al., "pH–Dependent Swelling and Solute Diffusion Characteristics of Poly (Hydroxyethyl Methacrylate–CO–Methacrylic Acid) Hydrogels," Pharm. Res., 1988, 5(9): 592–597.

Liu et al., "Trapidil in Preventing Restenosis After Balloon Angioplasty in the Atherosclerotic Rabbit," Circulation, 1990, 81: 1089–1093.

Lundergan et al., "Peptide Inhibition of Myointimal Proliferation by Angiopeptin, a Somatostatin Analogue," Am. J. Cardiol, 1991, 17(Supp. B): 132B–136B.

Majesky et al., "Heparin Regulates Smooth Muscle S Phase Entry in the Injured Rat Carotid Artery," Circ. Res., 1987, 61:296–300.

Marx et al., "Rapamycin–FKBP Inhibits Cell Cycle Regulators of Proliferation in Vascular Smooth Muscle Cells," Circ. Res., 1995, 76: 412–417.

Meyers et al., "Activation Mechanisms of Nucleoside Phosphoramidate Prodrugs," J. Med. Chem., 2000, 43: 4319–4327.

Nemecek et al., "Terbinfinc Inhibits the Mitogenic Response to Platelet–Derived Growth Factor in Vitro and Neointimal Proliferation in Vivo," J. Pharmacol. Exp. Thera., 1989, 1167–1174.

Okada et al., "Localized Release of Perivascular Heparin Inhibits Intimal Proliferation After Endothelial Injury Without Systemic Anticoagulation," Neurosurgery, 1989, 25: 892–898.

Peterson et al., "Superoxide Reduction of a Disulfide: A Model of Intracellular Redox Modulation?" Biochem. Biophys. Res. Comm., 1994, 200(3): 1586–1591.

Poon et al., "Rapamycin Inhibits Vascular Smooth Muscle Cell Migration," J. Clin. Invest., 1996, 98(10): 2277–2283.

Powell et al., "Controlled Release of Nerve Growth Factor from a Polymeric Implant," Brain Research, 1990, 515: 309–311.

Powell et al., "Inhibitors of Angiotensin–Coverting Enzyme Prevent Myointimal Proliferation After Vascular Injury," Science, 1989, 245: 186–188.

Radomsky et al., "Controlled Vaginal Delivery of Antibodies in the Mouse," Biology of Reproduction, 1992, 47: 133–140.

Saltzman et al., "Controlled Antibody Release from a Matrix of Poly(Ethylene–co–Vinyl Acetate) Fractionated with a Supercritical Fluid," J. of Appl. Polymer Science, 1992, 48: 1493–1500.

Saltzman et al., "Drugs Released from Polymers: Diffusion and Elimination in Brian Tissue," Chem. Eng. Science, 1991, 46:2429–2444.

Saltzman et al., "Transport Rates of Proteins in Porous Materials with Known Microgeometry," Biophysical J., 1989, 55: 163–171.

Sherwood et al., "Controlled Antibody Delivery Systems," Bio/Tech., 1992, 10: 1446–1449.

Siekierka, "Probing T–Cell Signal Transduction Pathways with the Immunosuppresive Drugs, FK–506 and Rapamycin," Immunol. Res., 1994, 13: 110–116.

Sigwart et al., "Prosthetic Coating—New Materials: Stent Coatings," J. Invasive Cardiol, 2001, 13(2): 141–142; discussion 158–170.

Snow et al., "Heparin Modulates the Composition of the Extrcellular Matrix Domain Surrounding Arterial Smooth Muscle Cells," Am. J. Pathol., 1990, 137(2): 313–330.

* cited by examiner

POLYMER COMPOSITIONS CONTAINING BIOACTIVE AGENTS AND METHODS FOR THEIR USE

CROSS REFERENCE TO RELATED APPLICATIONS

This application is related to U.S. patent application Ser. No. 09/123,930, which is a divisional application of U.S. Pat. No. 5,786,439 "HYDROPHILIC, SWELLABLE COATINGS FOR IMPLANTABLE DEVICES" and is related to U.S. Pat. No. 5,777,060 "SILICON CONTAINING BIOCOMPATIBLE MEMBRANES"; U.S. Pat. No. 5,391,250 "METHOD OF FABRICATING THIN FILM SENSORS"; and U.S. Pat. No. 5,390,671 "TRANSCUTANEOUS SENSOR INFUSION SET", the contents of each of which are incorporated herein by reference.

BACKGROUND OF THE INVENTION

1. Field of the Invention

The present invention relates to polymer compositions containing bioactive agents and methods for their use. Such compositions can be used to coat medical devices such as intravascular stents.

2. Description of Related Art

A wide variety of medical conditions are treated by introducing an implantable medical device partly or completely into the esophagus, trachea, colon, biliary tract, urinary tract, vascular system or other location within a human or veterinary patient. For example, many treatments of the vascular system entail the introduction of a device such as a stent, a catheter, a balloon, a wire guide, a cannula, or the like. However, when such a device is introduced into and manipulated through the vascular system, the blood vessel walls can be disturbed or injured. Clot formation or thrombosis often results at the injured site, causing stenosis or occlusion of the blood vessel. Moreover, if the medical device is left within the patient for an extended period of time, thrombus often forms on the device itself, again causing stenosis or occlusion. As a result, the patient is placed at risk of a variety of complications, including heart attack, pulmonary embolism, and stroke. Thus, the use of such a medical device can entail the risk of precisely the problems that its use was intended to ameliorate.

Another way in which blood vessels undergo stenosis is through disease. Probably the most common disease causing stenosis of blood vessels is atherosclerosis. Atherosclerosis is a condition which commonly affects the coronary arteries, the aorta, the iliofemoral arteries and the carotid arteries. Atherosclerotic plaques of lipids, fibroblasts, and fibrin proliferate and cause obstruction of an artery or arteries. As the obstruction increases, a critical level of stenosis is reached, to the point where the flow of blood past the obstruction is insufficient to meet the metabolic needs of the tissue distal to (downstream of) the obstruction. The result is ischemia.

Many medical devices and therapeutic methods are known for the treatment of atherosclerotic disease. One particularly useful therapy for certain atherosclerotic lesions is percutaneous translummnal angioplasty (PTA). During PTA, a balloon-tipped catheter is inserted in a patient's artery, the balloon being deflated. The tip of the catheter is advanced to the site of the atherosclerotic plaque to be dilated. The balloon is placed within or across the stenotic segment of the artery, and then inflated. Inflation of the balloon "cracks" the atherosclerotic plaque and expands the vessel, thereby relieving the stenosis, at least in part.

While PTA presently enjoys wide use, it suffers from two major problems. First, the blood vessel may suffer acute occlusion immediately after or within the initial hours after the dilation procedure. Such occlusion is referred to as "abrupt closure." Abrupt closure occurs in perhaps five percent or so of the cases in which PTA is employed, and can result in myocardial infarction and death if blood flow is not restored promptly. The primary mechanisms of abrupt closures are believed to be elastic recoil, arterial dissection and/or thrombosis. It has been postulated that the delivery of an appropriate agent (such as an antithrombic agent) directly into the arterial wall at the time of angioplasty could reduce the incidence of thrombotic acute closure, but the results of attempts to do so have been mixed. A second major problem encountered in PTA is the re-narrowing of an artery after an initially successful angioplasty. This re-narrowing is referred to as "restenosis" and typically occurs within the first six months after angioplasty. Restenosis is believed to arise through the proliferation and migration of cellular components from the arterial wall, as well as through geometric changes in the arterial wall referred to as "remodeling." It has similarly been postulated that the delivery of appropriate agents directly into the arterial wall could interrupt the cellular and/or remodeling events leading to restenosis. However, like the attempts to prevent thrombotic acute closure, the results of attempts to prevent restenosis in this manner have been mixed. Non-atherosclerotic vascular stenosis may also be treated by PTA. For example, Takayasu arteritis or neurofibromatosis may cause stenosis by fibrotic thickening of the arterial wall. Restenosis of these lesions occurs at a high rate following angioplasty, however, due to the fibrotic nature of the diseases. Medical therapies to treat or obviate them have been similarly disappointing.

A device such as an intravascular stent can be a useful adjunct to PTA, particularly in the case of either acute or threatened closure after angioplasty. The stent is placed in the dilated segment of the artery to mechanically prevent abrupt closure and restenosis. Unfortunately, even when the implantation of the stent is accompanied by aggressive and precise antiplatelet and anticoagulation therapy (typically by systemic administration), the incidence of thrombotic vessel closure or other thrombotic complication remains significant, and the prevention of restenosis is not as successful as desired. Furthermore, an undesirable side effect of the systemic antiplatelet and anticoagulation therapy is an increased incidence of bleeding complications, most often at the percutaneous entry site.

Other conditions and diseases are treatable with stents, catheters, cannulae and other devices inserted into the esophagus, trachea, colon, binary tract, urinary tract and other locations in the body, or with orthopedic devices, implants, or replacements. Consequently, it would be desirable to develop devices and methods for reliably delivering suitable agents, drugs or bioactive materials directly into a body portion during or following a medical procedure, so as to treat or prevent such conditions and diseases, for example, to prevent abrupt closure and/or restenosis of a body portion such as a passage, lumen or blood vessel. As a particular example, it would be desirable to have devices and methods which can deliver an antithrombic or other medication to the region of a blood vessel which has been treated by PTA, or by another interventional technique such as atherectomy, laser ablation, or the like.

There is a need in the art for improved compositions and methods that can be used with implantable medical devices to deliver bioactive agents at a site of implantation (e.g. a blood vessel which has been treated by PTA). Embodiments of the invention disclosed herein satisfy this need.

SUMMARY OF THE INVENTION

A discovery underlying the present invention is the incorporation of bioactive agents in polymer compositions, such as silicon containing siloxanes, in the formation of biocompatible coatings for medical devices such as stents. The polymer compositions can be used in conjunction with a variety of compounds for the preparation of coatings in which the movement of both endogenous and exogenous analytes and reactive species through the coatings (e.g., chemokines, immunosuppressive and/or anti-inflammatory agents) can be controlled. The coatings produced from these components are typically homogeneous and are useful for coating a number of devices designed for implantation.

The invention disclosed herein has a number of embodiments. A preferred embodiment of the invention is an implantable medical device having at least one polymer coating composition, the polymer coating prepared from a reaction mixture of a diisocyanate, the diisocyanate comprising about 50 mol % of the reactants in the mixture, a hydrophilic polymer which is a member selected from the group consisting of a hydrophilic polymer diol, a hydrophilic polymer diamine and combinations thereof, a bioactive agent; and optionally a chain extender. In preferred embodiments, the reaction mixture further comprises a siloxane polymer having functional groups at the chain termin, typically amino, hydroxyl and carboxylic acid groups. A specific embodiment of the invention includes a polymer coating having a water pickup of from about 25% to about 400% by weight. In yet another embodiment, the polymer coating has a glucose diffusion coefficient of from about $1 \times 10^{-9}$ cm$^2$/sec to about $200 \times 10^{-9}$ cm$^2$/sec, and a ratio of $D_{oxygen}/D_{glucose}$ of from about 5 to about 2000.

In illustrative embodiments of the invention, the diisocyanate used in the reaction mixture is selected from the group consisting of isophorone diisocyanate, 1,6-hexamethylene diisocyanate and 4,4'-methylenebis(cyclohexyl isocyanate). In embodiments of the invention that utilize a chain extender, preferably the chain extender is selected from the group consisting of an alkylene diol, an alkylene diamine, an aminoalkanol and combinations thereof. In a preferred embodiment of the invention, the diisocyanate is 1,6-hexamethylene diisocyanate, the hydrophilic polymer is selected from the group consisting of PEG 400 and PEG 600 and is present in an amount of about 17 to about 32 mol %, and the siloxane polymer is aminopropyl polysiloxane having a molecular weight of about 2000 to about 4000 and is present in an amount of about 17 to about 32 mol %.

A related embodiment of the invention is a polymer composition formed by admixing a diisocyanate, the diisocyanate comprising about 50 mol % of the reactants in the admixture, a hydrophilic polymer selected from the group consisting of a hydrophilic polymer diol, a hydrophilic polymer diamine and combinations thereof, a bioactive agent and optionally, a chain extender. Yet another embodiment of the invention is a method for making a polymer composition, the method comprising: admixing a diisocyanate, the diisocyanate comprising about 50 mol % of the reactants in the admixture, a hydrophilic polymer selected from the group consisting of a hydrophilic polymer diol, a hydrophilic polymer diamine and combinations thereof, a bioactive agent and, optionally, a chain extender, thereby forming the polymer composition.

In preferred embodiments of the invention, the bioactive agent is capable of being released from the polymer coating into the environment in which the medical device is placed. Moreover, as described herein, the reagents and reaction conditions of the polymer compositions can be manipulated so that the release of the bioactive agent from the polymer coating can be controlled. For example, the diffusion coefficient of the one or more polymer coatings can be modulated to control the release of the bioactive agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the bioactive agent from the polymer coating). Yet another embodiment of the invention includes a device having a plurality of polymer coatings, each having a plurality of diffusion coefficients. In such embodiments of the invention, the release of the bioactive agent from the polymer coating can be modulated by the plurality of polymer coatings.

In yet another embodiment of the invention, the release of the bioactive agent from the polymer coating is controlled by modulating one or more of the properties of the polymer composition such as the presence of one or more endogenous or exogenous compounds, or alternatively, the pH of the polymer composition. For example, certain polymer compositions disclosed herein can be designed to release a bioactive agent in response to a decrease in the pH of the polymer composition. Alternatively, certain polymer compositions disclosed herein can be designed release a bioactive agent in response to the presence of hydrogen peroxide.

Illustrative embodiments of the invention incorporate glucose oxidase into the polymer composition, a protein which reacts with glucose and oxygen to generate gluconolactone and hydrogen peroxide. The gluconolactone produced by this process then further reacts with water to hydrolyze the lactone ring and produce gluconic acid. A specific example of this embodiment of invention is an implantable medical device having at least one polymer coating composition, the polymer coating prepared from a reaction mixture of a diisocyanate, the diisocyanate comprising about 50 mol % of the reactants in the mixture, a hydrophilic polymer which is a member selected from the group consisting of a hydrophilic polymer diol, a hydrophilic polymer diamine and combinations thereof, glucose oxidase, a bioactive agent wherein the bioactive agent is capable of being released from the polymer coating into the environment in which the medical device is placed, and wherein the bioactive agent is an anti-thrombocytic, anti-inflammatory or anti-proliferative agent. In this embodiment, the release of the bioactive agent is modulated by a product that is produced from a reaction between the glucose oxidase that is present in the polymer coating and glucose (a typical analyte that facilitates the breakdown or hydrolysis of some portion of a polymer coating) that is present in the environment in which the medical device is placed. In a preferred embodiment the product that modulates the release of the bioactive agent is gluconic acid. Alternatively the product that modulates the release of the bioactive agent is hydrogen peroxide. Optionally a diffusion coefficient of one or more polymer coatings is manipulated to control the rate at which an analyte such as glucose diffuses through the polymer (thereby controlling the interaction between glucose and glucose oxidase).

A wide variety of medical devices can be coated with the polymer compositions disclosed herein. In preferred embodiments of the invention, the device is a stent, an infusion pump, a glucose sensor, a catheter, a balloon, a wire guide, a cannula or the like. In highly preferred embodiments, the device is an intravascular stent. In addition, a wide variety of bioactive agents can be incorporated into the polymer compositions disclosed herein. In preferred embodiments of the invention the bioactive agent is an anti-thrombocytic, anti-inflammatory or anti-proliferative agent. In highly preferred embodiments of the invention, the bioactive agent is rapamycin or heparin.

DETAILED DESCRIPTION OF THE PREFERRED EMBODIMENTS

Figure 1:
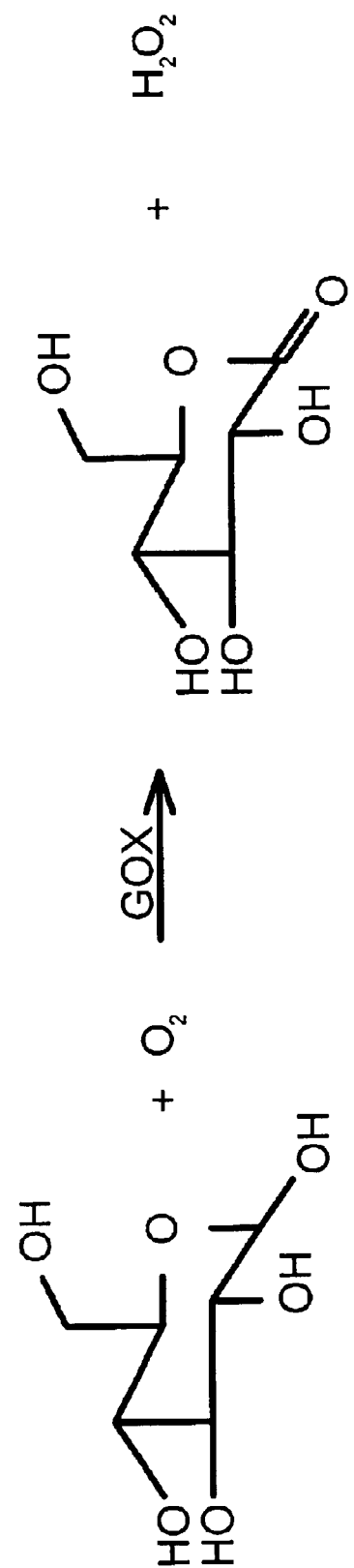
FIG. 1 provides a schematic of the chemical reaction between glucose and oxygen in the presence of glucose oxidase. In this reaction, glucose reacts with oxygen in the presence of glucose oxidase (GOX) to form gluconolactone and hydrogen peroxide. The gluconolactone further reacts with water to hydrolyze the lactone ring and produce gluconic acid.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as those described in see Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

Embodiments of the invention disclosed herein provide polymer compositions that include bioactive agents and which can be used in the formation of biocompatible coatings for medical devices such as stents. The properties of these polymer compositions can be modulated to generate coatings in which the movement of both endogenous and exogenous bioactive agents and analytes and through the coatings (e.g., saccharides, chemokines, immunosuppressive and/or anti-inflammatory agents and the like) can be controlled. The coatings produced from these components are useful for coating a number of devices designed for implantation. Various embodiments and aspects of the invention are described in detail below.

Through the specification, the following abbreviations are used: dl, deciliter; DEG, diethylene glycol; DMF, dimethyl formamide; PBS, phosphate buffered saline; THF, tetrahydrofuran; DI, deionized; PEG, poly(ethylene)glycol; mv, millivolts.

Polymer Composition Components
  A. Polymer Components

Embodiments of the invention described herein include various types of polymer coatings for implantable medical devices such as stents, cannulae, implantable devices and the like that include bioactive agents such as anti-inflammatory, anti-thrombocytic and/or antibiotic agents. Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

Embodiments of the polymer coatings for implantable medical devices include hydrogels. A hydrogel is a highly-interdependent, biphasic matrix consisting of a solid component (usually a polymer, and more commonly a highly cross-linked polymer) that has both hydrophilic and hydrophobic character. Additionally, the matrix has a liquid component (e.g., water) that is retained in the matrix by intermolecular forces. The hydrophobic character provides the matrix with a degree of water insolubility while the hydrophilic character affords water permeability. The polymer portion of the hydrogel will contain functionality which is suitable for hydrogen bonding (e.g., hydroxyl groups, amino groups, ether linkages, carboxylic acids and esters, and the like). Moreover, the affinity for water presented by the hydrogen bonding functionality must be of sufficient degree that the hydrated hydrogel will retain the water within its matrix even upon placement of the hydrogel in a hydrophobic medium such as an oil or lipid matrix. In addition to this binding of water within the hydrogel matrix, the hydrogel should allow water to flow through it when placed in an aqueous environment.

Hydrogels used in coating the implantable devices typically include a polyurea, a polyurethane or a polyurethane/polyurea combination. As used herein, the term "polyurethane/polyurea" refers to a polymer containing urethane linkages, urea linkages or combinations thereof. Typically, such polymers are formed by combining diisocyanates with alcohols and/or amines. For example, combining isophorone diisocyanate with PEG 600 and 1,4-diaminobutane under polymerizing conditions provides a polyurethane/polyurea composition having both urethane (carbamate) linkages and urea linkages. Such hydrogels are typically prepared from the reaction of a diisocyanate and a hydrophilic polymer, and optionally, a chain extender. The hydrogels can be extremely hydrophilic and can have a water pickup of from about 25% to about 400% by weight, more preferably from about 150% to about 400%.

The diisocyanates which are useful in this aspect of the invention are those which are typically used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6-hexamethylene diisocyanate (HDI), trimethyl-hexamethylene diisocyanate (TMDI), trans-1,4-cyclohexane diisocyanate (CHDI), 1,4-cyclohexane bis(methylene isocyanate) (BDI), 1,3-cyclohexane bis(methylene isocyanate) ($H_6$XDI), isophorone diisocyanate (IPDI) and 4,4'-methylenebis(cyclohexyl isocyanate) ($H_{12}$MDI). In preferred embodiments, the diisocyanate is an aliphatic diisocyanate, more preferably isophorone diisocyanate, 1,6-hexamethylene diisocyanate, or 4,4'-methylenebis (cyclohexyl isocyanate). A number of these diisocyanates are available from commercial sources such as Aldrich Chemical Company Milwaukee, Wis., USA) or can be readily prepared by standard synthetic methods using literature procedures.

The quantity of diisocyanate used in the reaction mixture for the present compositions is typically about 50 mol % relative to the combination of the remaining reactants. More particularly, the quantity of diisocyanate employed in the preparation of the present compositions will be sufficient to provide at least about 100% of the—NCO groups necessary to react with the hydroxyl or amino groups of the remaining reactants. For example, a polymer which is prepared using x moles of diisocyanate, will use a moles of a hydrophilic polymer (diol, diamine or combination), and b moles of a chain extender, such that x=a+b, with the understanding that b can be zero.

A second reactant used in the preparation of the swellable coatings described herein is a hydrophilic polymer. The hydrophilic polymer can be a hydrophilic diol, a hydrophilic diamine or a combination thereof. The hydrophilic diol can be a poly(alkylene)glycol, a polyester-based polyol, or a polycarbonate polyol. As used herein, the term "poly (alkylene)glycol" refers to polymers of lower alkylene glycols such as poly(ethylene)glycol, poly(propylene)glycol and polytetramethylene ether glycol (PTMEG). The term "polyester-based polyol" refers to a polymer in which the R group is a lower alkylene group such as ethylene, 1,3-propylene, 1,2-propylene, 1,4-butylene, 2,2-dimethyl-1,3-propylene, and the like. One of skill in the art will also understand that the diester portion of the polymer can also vary. For example, the present invention also contemplates the use of succinic acid esters, glutaric acid esters and the like. The term "polycarbonate polyol" refers those polymers having hydroxyl functionality at the chain termini and ether and carbonate functionality within the polymer chain. The alkyl portion of the polymer will typically be composed of C2 to C4 aliphatic radicals, or in some embodiments, longer chain aliphatic radicals, cycloaliphatic radicals or aromatic radicals. The term "hydrophilic diamines" refers to any of the above hydrophilic diols in which the terminal hydroxyl groups have been replaced by reactive amine groups or in which the terminal hydroxyl groups have been derivatized to produce an extended chain having terminal amine groups. For example, a preferred hydrophilic diamine is a "diamino poly(oxyalkylene)" which is poly(alkylene)glycol in which the terminal hydroxyl groups are replaced with amino groups. The term "diamino poly(oxyalkylene" also refers to poly(alkylene)glycols which have aminoalkyl ether groups at the chain termini. One example of a suitable diamino poly(oxyalkylene) is poly(propylene glycol) bis(2-aminopropyl ether). A number of diamino poly (oxyalkylenes) are available having different average molecular weights and are sold as Jeffamines™ (for example, Jeffamines 230, Jeffamine 600, Jeffamine 900 and Jeffamine 2000). These polymers can be obtained from Aldrich Chemical Company. Alternatively, literature methods can be employed for their synthesis.

The amount of hydrophilic polymer which is used in the present compositions will typically be about 10% to about 100% by mole relative to the diisocyanate which is used. Preferably, the amount is from about 50% to about 90% by mole relative to the diisocyanate. When amounts less than 100% of hydrophilic polymer are used, the remaining percentage (up to 100%) will be a chain extender.

Thus, in one group of embodiments, the reaction mixture for the preparation of polymer coatings will also contain a chain extender which is an aliphatic or aromatic diol, an aliphatic or aromatic diamine, alkanolamine, or combinations thereof. Examples of suitable aliphatic chain extenders include ethylene glycol, propylene glycol, 1,4-butanediol, 1,6-hexanediol, ethanolamine, ethylene diamine, butane diamine and 1,4-cyclohexanedimethanol. Aromatic chain extenders include, for example, para-di(2-hydroxyethoxy) benzene, meta-di(2-hydroxyethoxy)benzene, Ethacure 100™ (a mixture of two isomers of 2,4-diamino-3,5-diethyltoluene), Ethacure 300™ (2,4-diamino-3,5-di (methylthio)toluene), 3,3'-dichloro-4, 4'diaminodiphenylmethane, Polacute™ 740 M (trimethylene glycol bis(para-aminobenzoate)ester), and methylenedianiline. Incorporation of one or more of the above chain extenders typically provides the resulting biocompatible membrane with additional physical strength, but does not substantially alter the hydrophilicity of the polymer. In particularly preferred compositions, the chain extender is butanediol, ethylenediamine, 1,6-hexamethylenediamine, 1,2-diaminocyclohexane or isophorone diamine. In one group of preferred embodiments, the chain extender is present an amount of from about 10% to 50% by mole relative to the diisocyanate.

Preferred polymers of the invention include silicone polymers. Exemplary silicone polymers which are useful in the present invention are typically linear. Preferably, the silicone polymer is a polydimethylsiloxane having two reactive functional groups (i.e., a functionality of 2). The functional groups can be, for example, hydroxyl groups, amino groups or carboxylic acid groups, but are preferably hydroxyl or amino groups. In some embodiments, combinations of silicone polymers can be used in which a first portion comprises hydroxyl groups and a second portion comprises amino groups. Preferably, the functional groups are positioned at the chain termini of the silicone polymer. A number of suitable silicone polymers are commercially available from such sources as Dow Chemical Company (Midland, Mich., USA) and General Electric Company (Silicones Division, Schenectady, N.Y., USA). Still others can be prepared by general synthetic methods, beginning with commercially available siloxanes (United Chemical Technologies, Bristol. Pa., USA). For use in the present invention, the silicone polymers will preferably be those having a molecular weight of from about 400 to about 10,000, more preferably those having a molecular weight of from about 2000 to about 4000. The amount of silicone polymer which is incorporated into the reaction mixture will depend on the desired characteristics of the resulting polymer from which the biocompatible coating are formed. For those compositions in which a decreased analyte mobility is desired, a larger amount of silicone polymer can be employed. Alternatively, for compositions in which an increased analyte mobility is desired, smaller amounts of silicone polymer can be employed. Typically, the amount of siloxane polymer will be (e.g. for a stent) from 10% to 90% by mole relative to the diisocyanate. Preferably, the amount is from about 20% to 60% by mole relative to the diisocyanate.

In addition, certain aspects of the present invention include methods utilizing coatings that both provide an active agent at the site of implantation as well as provide additional functional activities such as a reduction electrode impedance of a implantable device, for example by utilizing a coating composition with an extremely hydrophilic polymer such as a hydrogel or a cellulose acetate.

As is known in the art, the polymer compositions described herein can be used as a scaffolding which can be manipulated to add additional polymer components, bioactive agents, reactive chemical groups and the like. Various polymers and bioactive agents that can be incorporated into the polymer composition scaffolding are described in detail below. In addition, polymers having organic acid functional groups (e.g. carboxylic acid or sulfonic acid) are illustrative embodiments of this aspect of the invention (see e.g. U.S. Pat. No. 6,231,600). In the present context the term "organic acid group" is meant to include any groupings which contain an organic acidic ionizable hydrogen, such as carboxylic and sulfonic acid groups. The expression "organic acid functional groups" is meant to include any groups which function in a similar manner to organic acid groups under the reaction conditions, for instance metal salts of such acid groups, particularly alkali metal salts like lithium, sodium and potassium salts, and alkaline earth metal salts like calcium or magnesium salts, and quaternary amine salts of such acid groups, particularly quaternary ammonium salts.

Polymer having organic acid functional groups, can be included in a first or subsequent aqueous coating composition, and can be selected with due regard for the nature of the substrate to be coated. Typically a polymer in a first coating composition will be selected from homo- and co-polymers including vinylic monomer units, polyurethanes, epoxy resins, and combinations thereof. A polymer in the first coating composition is preferably selected from polyurethanes, polyacrylates, polymethacrylates, poly-isocrotonates, epoxy resins, acrylate-urethane co-polymers, and combinations thereof having organic acid functional groups. In a particularly preferred embodiment of methods of the invention, a polymer in the first coating composition is selected from homo- and co-polymers having a substantial amount of organic acid functional groups in their structure, which may act as an internal emulsifier. A class of polyurethanes which may be used in the first coating composition are the so-called water-borne polyurethanes, among which are the so-called internally emulsified water-borne polyurethane containing carboxylic acid groups and/or sulfonic acid groups, optionally as salts of such groups, as internal emulsifiers are particularly preferred.

B. Bioactive Components

The polymer compositions and methods of making and using them that are described herein can be used to incorporate a wide variety of bioactive agents that are known in the art (see e.g., Sigwart et al., "Stent Coatings" J Invasive Cardiol 2001 Feb.;13(2):141–2; discussion 158–70; Chan et al., Update on Pharmacology for Restenosis, Curr Interv Cardiol Rep. 2001 May;3(2):149–155; and Hofma et al., Recent Developments in Coated Stents, Curr Interv Cardiol Rep. 2001 Feb.;3(1):28–36). In illustrative embodiments of the invention, the bioactive agent is an immunosuppressive agent such as rapamycin (also known as sirolimus), which is a potent immunosuppressive agent that inhibits smooth muscle cell (SMC) proliferation by blocking cell cycle progression. Alternative embodiments of the invention provide polymers including anti-inflammatory agents such as dexamethasone and/or corticosteroids such as methylprednisolone. Alternative embodiments of the invention provide polymers including paclitaxel, a microtubule-stabilizing drug shown to inhibit vascular smooth muscle cell migration and proliferation contributing to neointimal hyperplasia. Other embodiments of the invention provide polymers including polypeptides such as hirudin (preferably polypeptides conjugated to a polyol such as polyethylene glycol) which has antithrombotic and potentially antiproliferative effects. Alternative embodiments of the invention provide polymers including the prostacyclin analogue iloprost which also has antithrombotic and potentially antiproliferative effects. Alternative embodiments of the invention provide polymers including molecules such as phosphorylcholine and the like which can improve the biocompatibility of an implanted device via biomimicry.

Preferred embodiments of the invention include agents used to inhibit restenosis such as those described in U.S. Pat. No. 6,273,913. In particular, numerous agents are being actively studied as antiproliferative agents for use in restenosis and have shown some activity in experimental animal models. These include: heparin and heparin fragments (Clowes and Karnovsky, 265 Nature, 25–626, (1977); Guyton, J. R. et al. 46 Circ. Res., 625–634, (1980); Clowes, A. W. and Clowes, M. M., 52 Lab. Invest., 611–616, (1985); Clowes, A. W. and Clowes, M. M., 58 Circ. Res., 839–845 (1986); Majesky et al., 61 Circ Res., 296–300, (1987); Snow et al., 137 Am. J. Pathol., 313–330 (1990); Okada, T. et al., 25 Neurosurgery, 92–898, (1989) colchicine (Currier, J. W. et al., 80 Circulation, 11–66, (1989), taxol (ref), agiotensin converting enzyme (ACE) inhibitors (Powell, J. S. et al., 245 Science, 186–188 (1989), angiopeptin (Lundergan, C. F. et al., 17 Am. J. Cardiol. (Suppl. B); 132B–136B (1991), Cyclosporin A (Jonasson, L. et. al., 85 Proc. Natl, Acad. Sci., 2303 (1988), anti-PDGF antibody (Ferns, G. A. A., et al., 253 Science, 1129–1132 (1991), terbinafine (Nemecek, G. M. et al., 248 J. Pharmacol. Exp. Thera., 1167–11747 (1989), trapidil (Liu, M. W. et al., 81 Circulation, 1089–1093 (1990), interferon-gamma (Hansson, G. K. and Holm, 84 J. Circulation, 1266–1272 (1991), steroids (Colburn, M. D. et al., 15 J. Vasc. Surg., 510–518 (1992), see also Berk, B. C. et al., 17 J. Am. Coll. Cardiol., 111B–117B (1991), fusion toxins, antisense oligonucleotides, gene vectors, and rapamycin.

Of particular interest in rapamycin. Rapamycin is a macrolide antibiotic which blocks IL-2-mediated T-cell proliferation and possesses anti-inflammatory activity. While the precise mechanism of rapamycin is still under active investigation, rapamycin has been shown to prevent the $G_1$ to S phase progression of T-cells through the cell cycle by inhibiting specific cell cyclins and cyclin dependent protein kinases (Siekierka, Immunol. Res. 13: 110–116, 1994). The antiproliferative action of rapamycin is not limited to T-cells; Marx et al. (Circ Res 76:412–417, 1995) have demonstrated that rapamycin prevents proliferation of both rat and human SMC in vitro while Poon et al. have shown the rat, porcine, and human SMC migration can also be inhibited by rapamycin (J Clin Invest 98: 2277–2283, 1996). Thus, rapamycin is capable of inhibiting both the inflammatory response known to occur after arterial injury and stent implantation, as well as the SMC hyperproliferative response. In fact, the combined effects of rapamycin have been demonstrated to result in a diminished SMC hyperproliferative response in a rat femoral artery graft model and in both rat and porcine arterial balloon injury models (see, e.g. Gregory et al., Transplantation 55:1409–1418, 1993;). These observations clearly support the potential use of rapamycin in the clinical setting of post-angioplasty restenosis.

Although the ideal agent or agents for inhibiting restenosis have not yet been identified, some desired properties are clear: inhibition of local thrombosis without the risk systemic bleeding complications and continuous and prevention of the sequel of arterial injury, including local inflammation and sustained prevention smooth muscle proliferation at the site of angioplasty without serious systemic complications. Inasmuch as stents prevent at least a portion of the restenosis process, an agent which prevents inflammation and the proliferation of SMC combined with a stent may provide the most efficacious treatment for post-angioplasty restenosis.

In addition to those bioactive agents described above, suitable conventional pharmaceuticals or bioactive agents include, but are not limited to, antimicrobials, antibiotics, antimyobacterial, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, antiarthritics, and diagnostic agents. In certain aspects, the bioactive agent will be an antineoplastic agent, such as vincristine, doxorubicin, mitoxantrone, camptothecin, cisplatin, bleomycin, cyclophosphamide, methotrexate, streptozotocin, and the like. Antitumor agents include, for example, actinomycin D, vincristine, vinblastine, cystine arabinoside, anthracyclines, alkylative agents, platinum compounds, antimetabolites, and nucleoside analogs, such as methotrexate and purine and pyrimidine analogs.

The bioactive agents used in the polymers described herein can be prepared and/or modified according to a wide variety of techniques known in the art such as being encapsulated in liposomes. For example U.S. Pat. No. 6,200,599 teaches nucleic acids of all types may be associated with the compounds described therein and liposomes. These include DNA, RNA, DNA/RNA hybrids (each of which may be single or double stranded), including oligonucleotides such as antisense oligonucleotides, chimeric DNA-RNA polymers, and ribozymes, as well as modified versions of these nucleic acids wherein the modification may be in the base, the sugar moiety, the phosphate linkage, or in any combination thereof. In addition, these include synthetic oligonucleotides involved in the induction of the sequence-specific RNA interference (RNAi) activity in mammalian cells (see, e.g. Hohjoh, FEBS Lett 2002 Jun. 19;521(1–3): 195–9). Antisense oligonucleotides may be constructed to inhibit expression of a target gene such as one expressed by cells colonizing a stent matrix (e.g. c-myc, c-ras and the like). A preferred antisense oligonucleotide is c-myc specific "Resten-NG" as described in Kipshidze et al., J Am Coll Cardiol 2002 May 15;39(10):1686–91.

Liposome formulations can also be used to deliver a broad range of conventional pharmaceuticals and therapeutic drugs. In addition to the aforementioned nucleic acids, in certain aspects, the liposome formulations of the present invention comprise small organic or inorganic compounds as bioactive agents. In certain embodiments, the liposomal formulations can encapsulate a bioactive agent and then release the encapsulated contents upon mild acidic conditions. For example, U.S. Pat. No. 6,200,599, describes the release of encapsulated calcein upon lowering the pH. Thus, the liposomal formulations comprising a pH-sensitive compound can advantageously be used to entrap, release and deliver therapeutic agents.

In related embodiments, the formulations such as liposome formulations of the present invention can be used to deliver anti-infective agents. The compositions of the present invention can also be used for the selective delivery of other drugs including, but not limited to, local anesthetics, e.g., dibucaine and chlorpromazine; beta-adrenergic blockers, e.g., propranolol, timolol and labetolol; antihypertensive agents, e.g., clonidine and hydralazine; antidepressants, e.g., imipramine, amitriptyline and doxepin; anti-conversants, e.g., phenytoin; antihistamines, e.g., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents. Those of skill in the art will know of other agents suitable for use with the polymer formulations and methods of the present invention.

As discussed below, the bioactive agents may be entrapped within the polymer compositions or coupled to the polymer compositions using one or more the techniques for generating such compositions known in the art.

Preparation And Manipulation Of Polymer Compositions

The polymer coating preparations described herein can be prepared by methods typically employed in the art. For example, polymerization of the reactants can be carried out in bulk or in a solvent system. Use of a catalyst is preferred, though not required. Suitable catalysts include dibutyltin bis(2-ethylhexanoate), dibutyltin diacetate, triethylamine and combinations thereof. Preferably dibutyltin bis(2-ethylhexanoate is used as the catalyst. Bulk polymerization is typically carried out at an initial temperature of about 25° (ambient temperature) to about 50° C., in order to insure adequate mixing of the reactants. Upon mixing of the reactants, an exotherm is typically observed, with the temperature rising to about 90°–120° C. After the initial exotherm, the reaction flask can be heated at from 75° C. to 125° C., with 90° C. to 100° C. being a preferred temperature range. Heating is usually carried out for one to two hours. Polymers prepared by bulk polymerization are typically dissolved in dimethylformamide and precipitated from water. Polymers prepared in solvents such as THF can be poured into water at ambient temperatures, then filtered, dried, washed with boiling water and re-dried.

Solution polymerization can be carried out in a similar manner. Solvents which are suitable for solution polymerization include, tetrahydrofuran, dimethylformamide, dimethyl sulfoxide, dimaethylacetamide, halogenated solvents such as 1,2,3-trichloropropane, and ketones such as 4-methyl-2-pentanone. Preferably, THF is used as the solvent. When polymerization is carried out in a solvent, heating of the reaction mixture is typically carried out for at least three to four hours, and preferably at least 10–20 hours. At the end of this time period, the solution polymer is typically cooled to room temperature and poured into DI water. The precipitated polymer is typically collected, dried, washed with hot DI water to remove solvent and unreacted monomers, then re-dried. The dried polymer can be evaluated for water pickup as described for example in U.S. Pat. Nos. 5,786,439 and 5,777,060. In certain embodiments of the invention, the hydrogels of the invention will have a water pickup of at least 120%, preferably 150% to about 400%, and more preferably about 200% to about 400%. An illustrative embodiment of the invention includes a polymer coating having a water pickup of from about 25% to about 400% by weight. In a related embodiment, the polymer coating has a glucose diffusion coefficient of from about $1 \times 10^{-9}$ $cm^2$/sec to about $200 \times 10^{-9}$ $cm^2$/sec, and a ratio of $D_{oxygen}/D_{glucose}$ of from about 5 to about 2000, or optionally, from about 5 to about 200.

As discussed herein, the reactants and reaction conditions used to generate the polymer compositions disclosed herein can be modified to alter the properties of the final polymer composition. For example, properties such as the diffusion coefficients (e.g. the rate at which molecules such as endogenous and exogenous analytes are able to diffuse through the polymer matrix), the rate of degradation of one or more of the polymer components or the rates of the release of a bioactive agent(s) can be manipulated by manipulating the reaction conditions (and hence the final polymer composition properties) used to generate the polymers.

From the above description, it will be apparent to one of skill in the art that the discovery underlying the present invention is the use of polymer compositions such as silicon-containing polymers, such as siloxanes, which incorporate bioactive agents in the formation of biocompatible coatings. For example, silicon-containing polymers are used in conjunction with (e.g. covalently attached to) other compounds such as hydrophilic polymers, compounds having reactive groups and bioactive compositions for the preparation of coatings in which the movement of analytes and reactive species can be controlled by varying the amounts of each component. The coatings produced from these components are typically homogeneous and are useful for coating a number of devices designed for in vivo implantation. Once polymers have been prepared having suitable properties, the polymers can be solubilized in a solvent and used to coat a implantable device.

Preparation of coated implantable devices is typically accomplished by dissolving the dried polymer in a suitable solvent and spin-coating the medical device, typically using, for example, a 5 wt % /in 2-propanol solution of the polymer. The selection of other suitable solvents for coating the medical devices will typically depend on the particular polymer as well as the volatility of the solvent. Other suitable solvents include THF, $CHCl_3$, $CH_2Cl_2$, DMF or combinations thereof. More preferably, the solvent is THF or $DMF/CH_2Cl_2$.

A preferred method of modulating the properties of the polymer compositions disclosed herein is to control the diffusion coefficient (which relates to the rate at which a compound diffuses through a coating matrix) of the one or more polymer coating layers. In this context, analyte diffusion coefficients can be determined for the coating compositions of the present invention. Methods for determining diffusion coefficients are known to those of skill in the art, and are described for example in U.S. Pat. Nos. 5,786,439 and 5,777,060.

An illustrative method of coating a medical device includes sequentially applying a plurality of relatively thin outer layers of a coating composition comprising a solvent mixture of polymeric silicone material and crosslinker and, optionally a biologically active species (see, e.g. U.S. Pat. No. 6,358,556). The coatings can be cured in situ and the coated, cured prosthesis can be sterilized in a step that includes preferred pretreatment with argon gas plasma and exposure to gamma radiation electron beam, ethylene oxide, steam.

In this context, embodiments of the present invention provides processes for producing a relatively thin layer of biostable elastomeric material in which an amount of biologically active material is dispersed as a coating on the surfaces of a medical device such as a stent. The preferred stent to be coated is a self-expanding, open-ended tubular stent prosthesis. Although other materials, including polymer materials, can be used, in the preferred embodiment, the tubular body is typically formed of an open braid of fine single or polyfilament metal wire which flexes without collapsing and readily axially deforms to an elongate shape for transluminal insertion via a vascular catheter. The stent resiliently attempts to resume predetermined stable dimensions upon relaxation in situ.

The polymer coating is preferably applied as a mixture, solution or suspension of polymeric material and one or more biologically active species dispersed in an organic vehicle or a solution or partial solution of such species in a solvent or vehicle for the polymer and/or biologically active species. Optionally different biological species are placed within different polymer layers. The bioactive material(s) is dispersed in a carrier material which may be the polymer, a solvent, or both. The coating is preferably applied as one or more relatively thin layers that are applied sequentially. In some applications the coating may further be characterized as an undercoat and a topcoat. The coating thickness ratio of the topcoat to the undercoat may vary with the desired effect and/or the elution system. Typically these are of different formulations.

In an illustrative embodiment of a device having a plurality of coating layers, the coating on the medical device includes one or more base coatings and a top coating (see, e.g. U.S. Pat. No. 6,287,285). Optionally, the base coat has a binding component and a grafting component, and is used to adhere to the surface of the device and also to bond to the top coat. Specifically, the binding component binds to both the top coat and to the grafting component, and the grafting component adheres to the device surface. Typically, the base coat containing the grafting component and binding component in a suitable carrier such as a solution is first applied to the surface of the device. The base coat is preferably polymerized, e.g., exposed to polymerizing agent to polymerize the grafting component, and the grafting component is bonded to the binding component and adhered to the surface of the device to form a base coat on the device. The device is then coated with a top coat containing a desired bioactive agent. The top coat may be applied in a solution which is allowed to evaporate, to form a top coat with a bioactive agent. In another embodiment, the device is coated with a top coat comprising a linking agent, and the linking agent is exposed to the bioactive agent to form a complex therewith, to thereby form the bioactive coating of the invention. Because the top coat bonds to the base coat, the therapeutic, diagnostic, or hydrophilic coating produced will not readily wear off.

In one embodiment, the base coat comprises a binding component which is a homofunctional compound having homofunctional groups which covalently bond to functional groups in the top coat. In a preferred embodiment, the homofunctional binding component is grafted to the grafting component by a hydrogen abstraction mechanism, in which the grafting component is activated by initiators and covalently bonds to the binding component. In another embodiment, the base coat comprises a binding component which is a heterofunctional compound having a first functional group for covalently bonding with the grafting component, and a second functional group for covalently bonding to functional groups in the top coat.

As mentioned above, in such illustrative embodiments of the invention the binding component of the base coat bonds to the top coat. In a specific embodiment, a therapeutic, diagnostic, hydrophilic or other bioactive agent has functional groups which directly bond to functional groups of the binding component. In another embodiment, the bioactive agent is bound to the binding component by a linking agent in the top coat. The linking agent may inherently have functional groups, or may be modified to include functional groups, which bond to functional groups of the binding component. The linking agent may be bound to the base coat and thereafter exposed to the bioactive agent, or alternatively, the linking agent may be exposed to the agent before or during the binding of the linking agent to the base coat.

A variety of suitable linking agents may be used to encapsulate and/or link components of the polymer matrix (e.g. the different polymers that comprise the various coating layers, the bioactive agents in the polymer matrices etc), including avidin-biotin complexes, and functionalized liposomes and microsponges and microspheres. Avidin is a polypeptide composed of at least 128 amino acid residues. Typically however, the single polypeptide chain is a subunit associated with three essentially identical polypeptide chains, forming a teamster. Avidin as a receptor is typically used in conjunction with its highly specific ligand, biotin, $C_{10}H_{16}N_2O_3S$. An avidin tetramer will bind 4 biotin molecules in solution in a noncovalent interaction which has a binding constant of about $10^{15}$ $M^{-1}$, a half-life in vivo of about 89 days, and which is essentially undisturbed by organic solvents. Biotinylation, or the process of covalently binding biotin to another molecule, typically takes place by N-hydroxysuccinimide binding. Spacer molecules may be inserted between the avidin and the base coat, or between the biotin and the therapeutic or diagnostic agent, as is known in the art, to facilitate avidin-biotin binding or improve the activity of the therapeutic or diagnostic agent. The avidin or the biotin molecule may be chemically altered to decrease the binding constant, to thereby tailor the dissociation rate in vivo, and provide controlled release of the therapeutic or diagnostic agent bound thereto. Avidin and biotin are available from a variety of commercial suppliers, such as Sigma. In one embodiment, avidin covalently binds to the binding component of the base coat, and binds to a biotinylated therapeutic or diagnostic agent, such as a biotinylated protein, small molecule, peptide or oligonucleotide. However, the avidin-biotin linking agent may alternatively have biotin moieties covalently bound to the binding component of the base coat, and avidin moieties bound to the therapeutic or diagnostic agent. Alternatively, biotin may be covalently bound to the base coat and to the therapeutic or diagnostic agent, with avidin, by virtue of its multivalency with biotin, binding the two biotin moieties together.

Embodiments of the invention include devices having a plurality of coating layers having a plurality of therapeutic agents. In one such embodiment, a first therapeutic agent (e.g. an antiproliferative, non-thrombogenic or anti-inflammatory agent) is preferably mixed with the polymer, water, and crosslinking agent to form an aqueous dispersion or emulsion. The polymeric emulsion or dispersion is then applied to the substrate to be coated and allowed to dry. A preferred method of drying is air drying. A second coating can be prepared by dissolving a second therapeutic agent (e.g. an antiproliferative, non-thrombogenic or anti-inflammatory agent) in water. In a preferred embodiment, the second agent is heparin. In one method, the stent or article having the first dried coating is dipped in the heparin solution, taken out and allowed to air dry. The finished coating is subject to ambient temperature or elevated temperature drying in order to allow the heparin to bond to the polymer layer of the first coating composition.

Some methods according to the present invention are effective at relatively low temperatures, and particularly at ambient or room temperature, to allow for use with heat sensitive substrates, pharmaceutical agents and biomolecules. In one embodiment of the method according to the invention, the functional groups of the crosslinking agent are capable of reacting with the organic acid functional groups of the polymer in the first coating composition and the organic acid functional groups of the second coating at a temperature in the range of 10° C.–70° C., preferably at a temperature in the range of 15° C.–35° C. Such reactivity of the crosslinking agent makes it possible to coat the substrate at a temperature in the range of 10° C.–70° C., for example at a temperature in the range of 15° C.–35° C., such as at room temperature, although, of course, higher drying temperatures can be used if desired. The drying time will depend on the drying temperature, higher drying temperatures requiring shorter drying time and vice versa. However, it will be within the ordinary skill of a person skilled in the art to determine a suitable combination of drying temperatures and drying time for a specific coating.

One embodiment of the invention is a water insoluble polymeric layer having a first therapeutic agent admixed therein and able to be released under physiological temperature and pH. This embodiment of the invention also contains the crosslinking agent bonded to the polymeric material and having a substantial number of active functional groups remaining and capable of bonding additional material to the first layer. In one embodiment, the aqueous dispersion or emulsion includes polyurethane, sirolimus, and polyfunctional aziridine. A second coating or layer can be added to the first layer by preparing an aqueous solution or emulsion, optionally one that contains a second therapeutic agent capable of being bound by the crosslinking agent. The second therapeutic agent is preferably a non-thrombogenic agent. A preferred non-thrombogenic agent includes heparin. After the application of the second therapeutic agent, the second layer is allowed to dry. While sirolimus and heparin are discussed as illustrative embodiments, artisans will understand that other bioactive agents can be used in such contexts.

According to the certain embodiments of the invention disclosed herein, bioactive agents are modified by chemically linking them to a high molecular weight, water-soluble polymer carrier. This modified agent is termed herein an agent-polymer conjugate. One special property of the agent conjugate is that the chemical linkage of the agent to the water-soluble polymer can be manipulated to hydrolytically degrade, thereby releasing biologically active agent into the environment in which they are placed.

The agent-polymer conjugates can be incorporated into a controlled release matrix, formulated from a second biocompatible polymer. When implanted into a tissue such as the intravascular space, the controlled-release matrix will release the agent-polymer conjugate which will release free agent molecules to treat the area of the tissue in the immediate vicinity of the polymer. The agent-polymer conjugates will also diffuse within the tissue, reaching a great distance from the matrix because of their low rate of clearance from the tissue. As the agent conjugates diffuse, the bond between the polymer and the agent will slowly degrade in a controlled, prespecified pattern, releasing the active agent into the environment in which they are placed to have its therapeutic effect. Similarly, agent-polymer conjugates can be administered directly to a tissue and the elimination rate will be reduced relative to free agent.

There are several important variables, all of which can be controlled to produce a final product that is best suited for treating a certain disease with specific kinds of agents. A first variable involves how the size and characteristics of the water-soluble polymer carrier can be varied. Either synthetic or naturally occurring polymers may be used. While not limited to this group, some types of polymers that might be used are polysaccharides (e.g. dextran, ficoll), proteins (e.g. poly-lysine), poly(ethylene glycol), or poly(methacrylates). Different polymers, because of their different size and shape, will produce different diffusion characteristics in the target tissue or organ.

Another variable is the specific nature of the hydrolytically labile bond between the water-soluble polymer and the agent (which, as is known in the art, can be varied). While not wishing to be limited to the following bonds, artisans can bond agents to water-soluble polymers using covalent bonds, such as ester, amide, amidoester, and urethane bonds. Artisans can also utilize ionic conjugates. By changing the nature of the chemical association between water-soluble polymer and agent, the half-life of carrier-agent association can be varied. This half-life of the agent-polymer conjugate in the environment in which it is placed can determine the rate of active agent release from the polymer and, therefore, the degree of penetration that the agent-polymer conjugate can achieve in the target tissue. Other suitable hydrolytically labile bonds which can be used to link the agent to the water soluble polymer include thioester, acid anhydride, carbamide, carbonate, semicarbazone, hydrazone, oxime, iminocarbonate, phosphoester, phophazene, and anhydride bonds.

The rate of hydrolytic degradation, and thus of agent release, can be also altered from minutes to months by altering the physico-chemical properties of the bonds between the agents and the polymer. The rate of release can be affected by (a) the nature of the bond, e.g., ionic, thioester, anhydride, ester, and amide links, in order of decreasing lability; (b) stereochemical control, building in varying amounts of steric hindrance around the bonds which are to be hydrolyzed; (c) electronic control, building in varying electron donating/accepting groups around the reactive bond, controlling reactivity by induction/resonance; (d) varying the hydrophilicity/hydrophobicity of spacer groups between the agent and the polymer; (e) varying the length of the spacer groups, increasing length making the bond to be hydrolyzed more accessible to water; and (f) using bonds susceptible to attack by enzymes present in the environment in which the device is placed.

Another variable is the how the properties of the controlled release matrix can be varied, according to methods described in the art to vary the rate of polymeric agent conjugate release into the tissue (see, e.g. Saltzman, et al., 1991, Chemical Engineering Science, 46:2429–2444; Powell, et al., 1990, Brain Research, 515:309–311; Dang, et al., 1992, Biotechnology Progress,8:527–532; Saltzman, et al., 1989, Biophysical Journal, 55:163–171; Radomsky, et al., 1992, Biology of Reproduction, 47:133–140; Saltzman, et al., 1992, Journal of Applied Polymer Science, 48:1493–1500; Sherwood, et al., 1992, Bio/Technology, 10: 1446–1449). Among the variables which affect conjugate release kinetics are: controlled release polymer composition, mass fraction of agent-polymer conjugate within the matrix (increasing mass fraction increases release rate), particle size of agent-polymer conjugate within the matrix (increasing particle size increases release rate), composition of polymeric agent conjugate particles (which can be varied by adding free agent agents or inert agents that influence particle solubility), and size (increasing surface area increasing the release rate), and shape (changing the pattern, e.g., first order, zeroth order, etc.) of the controlled release matrix. Suitable polymer components for use as controlled-release matrices include poly(ethylene-co-vinyl acetate), poly(DL-lactide), polyglycolide), copolymers of lactide and glycolide, and polyanhydride copolymers.

A preferred embodiment of the invention includes the conjugation of a bioactive agent to a polymer via a hydrolytically labile bond to increase agent retention in a tissue, and, therefore increase the penetration distance of the bioactive agent in the tissue (see, also U.S. Pat. No. 6,545,681). Typically the bioactive agent conjugate is administered in a controlled-release matrix which comprises a biocompatible second polymer. Optionally the first polymer is water-soluble and the second polymer is not water-soluble. In this context, the polymer compositions of the invention comprise a polymer containing a functional group containing at least one hydrolyzable bond. Such polymer compositions include homo- and co-polymers and blends thereof (a copolymer or blend includes at least one other polymer which may or may not contain hydrolyzable bonds). By "hydrolyzable," "hydrolysis," and the like is meant the ability of water to chemically react with a substance to form two or more new substances. This typically involves ionization of the water molecule as well as splitting of the compound being hydrolyzed, e.g., an ester group of a polyester is hydrolyzed into the corresponding carboxylic acid and alcohol. By "acid-hydrolyzable bonds" and "base-hydrolyzable bonds" it is meant that the hydrolysis of the bond is initiated or catalyzed by an acidic or basic material, respectively. A bond may be both acid and base hydrolyzable. In addition, both types of bonds may be present in the polymer composition. The functional group containing hydrolyzable bonds may be present in the linear portions of the polymer chain (i.e., internal groups) or may be pendant to the polymer chain.

Exemplary functional groups which contain acid-hydrolyzable bonds include ortho-ester and amide groups. Exemplary functional groups which contain base-hydrolyzable bonds include α-ester and anhydride groups. Functional groups which contain both acid- and base-hydrolyzable bonds include carbonate, ester, and iminocarbonate groups. Thus, such exemplary polymers for use in the polymer compositions of the invention include polyesters, cellulose esters, polyester polyurethanes, polyamides, polycarbonates, and polyamino acids. A variety of other functional groups which contain labile bonds are known in the art and can be readily employed in the methods and compositions described herein (see, e.g. Peterson et al., Biochem. Biophys. Res. Comm. 200(3): 1586–1591 (1994) and Freel et al., J. Med. Chem. 43: 4319–4327 (2000)).

Optionally, the polymer composition further comprises pH-modifying compound. Optionally, the pH-modifying compound is a substantially water-insoluble. By "pH-modifying" is meant the ability of the compound to change the pH of an aqueous environment when the compound is placed in or dissolved in that environment. The pH-modifying compound is capable of accelerating the hydrolysis of the hydrolyzable bonds in the polymer upon exposure of the polymer composition to moisture and optionally heat. Suitable substantially water-insoluble pH-modifying compounds include substantially water-insoluble acids and bases. Inorganic and organic acids or bases may be used.

A variety of compositions and methods known in the art can be used to generate the compositions having functional groups which contain acid-hydrolyzable bonds disclosed herein. For example, in certain aspects, the present invention provides ortho ester lipids, and derivatives thereof, which upon certain pH conditions, undergo hydrolysis with concomitant or subsequent head group cleavage. As such, the present invention provides polymer compounds which include the compounds of Formula I as shown in U.S. Pat. No. 6,200,599. The compounds of Formula I typically comprise an ortho ester functionality or a derivative thereof. In general, ortho ester functionalities are among the most sensitive moieties toward acid-induced hydrolysis, more acid labile than for instance, acetals or enol-ethers. Although the ortho esters of this embodiment of the invention are preferably bicyclic in nature, the compounds of Formula I are not limited as such. Preferably, upon a decrease in pH, the ortho esters of the present invention are (i) hydrolyzed and thereafter undergo (ii) intramolecular transesterification with concomitant or subsequent headgroup cleavage. In certain instances, such as when $R^2$ is an alkoxy group and $R^3$ is hydrogen, compounds of Formula I are not bicyclic. However, these compounds retain their 'self-cleaving' feature and ability to participate in the 2-step decomposition process discussed above. In Formula I, A and $A^1$ can be the same or different heteroatom. By changing the nature of the heteroatoms making up the ortho ester functionality, (e.g., replacing an oxygen atom with a sulfur atom) the ortho esters become susceptible to hydrolysis at varying pH. Thus, it is possible to tailor or program the pH value where hydrolysis of the ortho ester will occur. Moreover, incorporation of sulfur enables oxidative means of ortho ester hydrolysis via sulfoxide or sulfone intermediates.

As discussed in U.S. Pat. No. 6,300,458, hydroxypolycarbonates (HPC) offer to the biomedical area additional hydroxyl functional polymers that bind bioactive agents or carbohydrate polymers chemically or via hydrogen bonding to facilitate agent delivery and utility with subsequent biodegradability to acceptable byproducts. In a specific embodiment, the cyclic carbonate (CC) from the monoketal diol of pentaerythritol polymerized in $CHCl_3$ at 60° C. with $Et_2$ Zn catalyst in $CHCl_3$ at 60° C. in 4 hours to a quantitative yield of high molecular weight, crystalline polymer (PCC), melt peak 199° C. and Tg of 99° C. PCC is readily hydrolyzed with 80% acetic acid to the water-insoluble but water-swollen HPC, poly[5,5-bis(hydroxymethyl)-1,3-dioxan-2-one], with $M_w=3.1\times10^4$. HPC degrades completely in vitro in <16 hours in PBS-1×buffer (Ph 7.4, 37° C.) to pentaerythritol and presumably $CO_2$. This rapid degradation rate is decreased with random copolymers of HPC with CC, $\epsilon$-caprolactone, or L-lactide. HPC and PCC may have important biomaterial applications as is and as the copolymers noted above or with ethylene oxide or other desirable comonomers. PCC and CC copolymers have properties attractive to the biomedical area as is or by conversion to the HPC product provided by hydrolysis or by in vivo enzymatic attack.

In this context, embodiments of the present invention include high weight average molecular weight (>5,000) polymers and copolymers of 5,5-bis(hydroxymethyl) 1,3-dioxan-2-one (hereinafter referred to as "BHMDO") and processes for manufacturing these polymers and copolymers. These polymers are biocompatible and useful for a variety of biomedical applications. Such homopolymers are crystalline and have a high melting point (ca 160–190° C.) which provides excellent mechanical properties. At the same time, they are hydrophilic and swellable by water (ca 100% at 37° C.), thereby enhancing biodegradability. The hydroxyl groups permit easy modification, an important advantage over non-hydrophilic biopolymers. For example, one can chemically bond a agent by an appropriate hydroxyl group reaction to form a hydrolytically labile bond or with a small peptide link cleavable by body enzymes along with a chemically bonded bioactive agent to target the anatomy with the appropriate agent. The hydroxyl groups provide hydrogen bonding with carbohydrate polymers, including nucleic acids, and proteins, which also facilitate direction of these polymers, as is or modified, to specific cites for therapeutic purposes. Properties can be varied widely via copolymers (generally from about 1% up to about 99% BHMDO) to change properties and permit diverse biomedical applications.

Related embodiments of the present invention provide erodible yet biocompatible polymers with desirable mechanical properties. In this context, the polymers HPC and PLC may also be attractive materials for temporary scaffolds or coatings. A feature of these polymers is their tendency to undergo surface erosion. Heterogeneous hydrolysis theoretically would better preserve the mechanical strength and physical integrity of the matrix during biodegradation, which is highly desirable in terms of predictable performance. To maximize control over the release process, it is desirable to have a polymeric system which degrades from the surface and deters the permeation of the agent molecules. Achieving such a heterogeneous degradation requires the rate of hydrolytic degradation on the surface to be much faster than the rate of water penetration into the bulk. A preferable embodiment is a polymer composition having a hydrophobic backbone and a water labile linkage.

As noted above, the polymer compositions disclosed herein allow for the controlled release of bioactive agents. This controlled release can be modulated by a number of factors including the diffusion coefficient of the polymer matrix as well as the pH of the environment in which the polymer compositions function. In this context, one of the embodiments of the invention includes a method for the controlled release of a biologically active agent wherein the agent is released from a hydrophobic, pH-sensitive polymer matrix (see also U.S. Pat. No. 6,306,422). In one embodiment, a polymer of hydrophobic and weakly acidic comonomers is disclosed for use in the controlled release system. In a specific embodiment, weakly basic comonomers are used and the active agent is released as the pH drops. For example a medical device coated with a pH-sensitive polymer having an antibiotic trapped within its matrix can release the active agent when exposed to a higher pH environment as the polymer gel swells. Such release can be made slow enough so that the bioactive agent remains at significant levels for a clinically useful period of time.

Related embodiments of the invention provide additional compositions and method for releasing a bio-active agent or a agent within a biological environment in a controlled manner. One such composition is a dual phase polymeric agent-delivery composition comprising a continuous biocompatible gel phase, a discontinuous particulate phase comprising defined microparticles and an agent to be delivered (see, e.g. U.S. Pat. No. 6,287,588). Typically in such embodiments, a microparticle containing a bio-active agent is releasably entrained within a biocompatible polymeric gel matrix. The bio-active agent release may be contained in the microparticle phase alone or in both the microparticles and the gel matrix. The release of the agent is prolonged over a period of time, and the delivery may be modulated and/or controlled. In addition, a second agent may be loaded in some of the microparticles and/or the gel matrix.

In such embodiments of the invention, a main mechanism of in vivo degradation of the polymers is by hydrolytic degradation in which endogenous enzymes may also play a role (see, e.g. Meyers et al., J. Med. Chem. 2000, 43, 4319–4327). Important factors influencing hydrolytic degradation include water permeability, chemical structure, molecular weight, morphology, glass transition temperature, additives, and other environmental factors such as pH, ionic strength, site of implantation, etc. The duration of sustained delivery can be adjusted from few days up to one year by a person of ordinary skill in the art through proper selection of polymer and fabrication method.

Embodiments of the invention include those in which the release of one or more biologically active agents is multiphasic. For example, this release can comprise an initial burst or, immediate release of an agent present at or near the surface of the coating layer, a second phase during which a release rate is slow or sometime no bio-active agent is released, and a third phase during which most of the remainder of the biologically active agent (or another bio-active agent) is released as erosion proceeds. Any agent, as long as it is suitable for incorporation into a polymer matrix (e.g. via microencapsulation in a microparticle), as is known in the art, can utilize the delivery system described by the current invention.

Specific embodiments of the invention include bioactive agents that are incorporated in microparticles. Since the polymeric gel and/or microparticle of the delivery system of the invention are preferably biocompatible and biodegradable, there is minimal toxic effect and irritation to the host. The agent release profile can be controlled and improved by proper design and preparation of various gel forming polymers or copolymer blocks. The release profile of the polymeric gel may also be modified through preparation of a gel blend by selection of individual gel systems and ratios of individual gel systems in the blend. Agent release is also controllable through adjustment of the concentration of the gel blends in the agent delivery liquid. Additional or second agents can also be loaded into the microparticles and/or the polymeric gel matrix. The additional agent can be a regulatory agent for the microparticle and/or the gel, or a second bio-active agent to be released into the biological environment in a same or different release rate. In such embodiments, a consideration as to how much agent can be loaded into the microparticle and how much of such agent carrying microparticle can be loaded into the polymeric gel is one of functionality, namely, the agent/microparticle load may be increased until the microparticle structure, and/or the gelation properties of the polymer or copolymer are adversely affected to an unacceptable degree, or until the properties of the system are adversely affected to such a degree as to make administration of the system unacceptably difficult. Generally speaking, about 0.0001 to 30% by weight of an agent can be loaded into a microparticle with 0.001 to 20% being most common. The agent carrying microparticle will generally make up between 0.0001 to 30% by weight of the formulation with ranges of between about 0.001 to 20% being most common. These ranges of agent/microparticle loading are not limiting to the embodiments of the invention. Provided functionality is maintained, agent loadings outside of these ranges fall within the scope of the invention.

As noted above, this invention is applicable to bio-active agents of all types including oligonucleotides, small molecules, growth inhibitory agents, and it offers an unusually effective way to deliver polypeptides and proteins. The only limitation to the polypeptide or protein drug which may be utilized is one of functionality. In some instances, the functionality or physical stability of polypeptides and proteins can also be increased by the addition of various additives to aqueous solutions or suspensions of the polypeptide or protein agent. Additives, such as polyols (including sugars), amino acids, surfactants, polymers, other proteins and certain salts may be used. These additives can readily be incorporated into the microparticle/polymer gel system of the present invention, which will then undergo a gelation process.

In addition to the microparticles disclosed above, additional agents such as liposomes can be used to control the release of bioactive agents from the disclosed polymer compositions. Liposomes are lipid molecules formed into a typically spherically shaped arrangement defining aqueous and membranal inner compartments. Liposomes can be used to encapsulate compounds such as therapeutic and diagnostic agents within the inner compartments, and deliver such agents to desired sites within a patient. The agents contained by the liposome may be released by the liposome and incorporated into the patient's cells, as for example, by virtue of the similarity of the liposome to the lipid bilayer that makes up the cell membrane. A variety of suitable liposomes may be used, including those available from NeXstar Pharmaceuticals or Liposome, Inc., if functionalized as by the procedures described herein.

In addition to liposomes, microsponges can be used to control the release of bioactive agents from the disclosed polymer compositions. Microsponges are high surface area polymeric spheres having a network of cavities which may contain compounds such as therapeutic or diagnostic agents. The microsponges are typically synthesized by aqueous suspension polymerization using vinyl and acrylic monomers. The monomers may be mono or bifunctional, so that the polymerized spheres may be cross-linked, thus providing shape stability. Process conditions and monomer selection can be varied to tailor properties such as pore volume and solvent swellability, and the microsponges may be synthesized in a controlled range of mean diameters, including small diameters of about 2 micrometers or less. A standard bead composition would be a copolymer of styrene and di-vinyl benzene (DVB). The agents contained by the polymeric microsponges may be gradually released therefrom within the patient due to mechanical or thermal stress or sonication. A variety of suitable microsponges may be used, including those available from Advanced Polymer Systems, if functionalized as by the procedures described herein.

An alternative embodiment includes a device containing reservoirs loaded with the bioactive agent (see, e.g. U.S. Pat. No. 6,273,913). In such embodiments, a polymer coating of the invention is applied over the reservoirs to control the diffusion of the drug from the reservoirs to the desired site within the body (e.g. the artery wall). One advantage of this system is that the properties of the coating can be optimized for achieving superior biocompatibility and adhesion properties, without the addition requirement of being able to load and release the drug. The size, shape, position, and number of reservoirs can be used to control the amount of drug, and therefore the dose delivered.

Yet another embodiment of the invention utilizes oscillating chemical systems to modulate the release of bioactive agents (see, e.g. U.S. Pat. No. 6,068,853). By taking advantage of oscillating chemical systems, one can change the state, i.e. the pH, of a solution, a bioactive drug, enhancer or solubilizer resulting in oscillating the ability of an active ingredient to be delivered. The pH of a solution can be oscillated over a range of pH values from 2 to 10 by the reduction and oxidation (redox) reactions of salts, such as permanganates, iodates, sulfates, chlorates, or bromates. Upon activation, the delivery system conditions begin to oscillate and with it, the delivery of the active agent oscillates.

In general, the present invention control of an active agent can be seen with specific reference to pH and/or redox oscillating reactions. However, any other oscillating species in an oscillating reaction can advantageously be employed in a similar fashion. With reference to oscillating systems in pharmaceutical contexts, the environment of the active agent to be delivered can have its state, i.e. pH, altered between a value where the active agent shifts between species which more readily and less readily permeates or diffuses through a delivery device barrier; a membrane barrier through which the active agent must pass or a matrix from which the active agent must be released can have its permeability altered in response to oscillation changes; a barrier separating a flux enhancer from the active agent can be modulated to regulate the amount of flux enhancer delivered to the active agent and as a result modulate the flux enhancer dependent active agent delivery; a polymer can be modulated to shift between a more viscous and less viscous form (i.e. poly-.gamma.-glutamate as in Creacenzi et al., Polymer Preprints, August 1994, 407–408) or a more solubilized and less solubilized form or a more swollen and a less swollen form (i.e. poly(meth)acrylic acid as in Kou et al., Pharmaceutical Research 5, #1988, 592–597), thereby altering the amount of water available to the active agent or another membrane which either needs to be or needs not to be hydrated in order to have proper active agent delivery, etc.

Where a lipophilic membrane is involved, either as part of the delivery device or as a membrane of the patient through which the active agent must pass (and is not changed by the environment through which it passes after leaving the device and before arriving at the lipophilic membrane), the combination of an active agent, preferably a agent, with a chemical oscillating reaction, may render the active agent charged or uncharged relative to its own pKa value. Since only the uncharged form of a drug can permeate across lipophilic membranes, a periodic delivery profile may be obtained by oscillating the state, i.e. pH, of the drug solution. The same type of end result can be achieved by oscillating the permeability of a membrane to either the active agent per se or to a flux enhancer needed for active agent delivery.

Exemplary Coated Devices

The polymer compositions of the present invention are useful with a variety of implantable devices. The present invention depends not on the configuration of the implantable device, but rather on the use of the inventive membranes to cover or encapsulate the device elements. Preferred embodiments of the present invention include a therapeutic, biocompatible coating over a device substrate. One article suitable for incorporating the present invention is a stent suitable for implantation within a body vessel such as a coronary blood vessel. A preferred stent made according to the present invention includes a first, restenosis inhibiting therapeutic agent admixed in a polymeric layer which together coat the stent and a second, non-thrombogenic therapeutic agent coating the first coating. Substrates suitable for incorporating the present invention include, for example, plastics, other polymeric materials, metals, metallic wires, glass and ceramics. A preferred apparatus incorporating the present invention is a stent, in particular a coronary artery stent formed of a metallic material such as Nitinol or stainless steel.

In an illustrative embodiment of the invention, a device such as a stent is provided with a hybrid coating including a time released, restenosis inhibiting coating and a non-thrombogenic coating to prevent clotting on the device. A first coat or layer includes a polymer, a crosslinking agent, and pacitaxel, analogues, or derivatives thereof The first coat preferably includes a polymer having a bioactive agent admixed therein so as to be releasable over time. The first coat can include a crosslinking agent. The second coat preferably includes an agent such as heparin to inhibit clot formation on the device. The crosslinking agent can covalently bond to both the first coat polymer and the second coat. A stent can be provided with a first coat including an aqueous dispersion or emulsion of a polymer and an excess of crosslinking agent. The first coating can be dried, leaving a water insoluble polymer coating. A second aqueous coating including a solution or dispersion of heparin can be applied over the first coating, the heparin becoming covalently bound to the crosslinking agent on the first coating surface. The resulting stent can inhibit restenosis while preventing blood clot formation on the stent.

The hydrogels described herein are particularly useful with a variety of implantable devices for which it is advantageous to provide a surrounding water layer. Glucose sensors which utilize, for example, glucose oxidase to effect a reaction of glucose and oxygen are known in the art, and are within the skill in the art to fabricate. See, for example, U.S. Pat. Nos. 5,165,407, 4,890,620, 5,390,671 and 5,391,250, the disclosures of each being incorporated herein by reference. For example, sensors for monitoring glucose concentration of diabetics are described in Shichiri, et al.,: "In Vivo Characteristics of Needle-Type Glucose Sensor-Measurements of Subcutaneous Glucose Concentrations in Human Volunteers," Horm. Metab. Res., Suppl. Set. 20:17–20 (1988); Bruckel, et al.,: "In Vivo Measurement of Subcutaneous Glucose Concentrations with an Enzymatic Glucose Sensor and a Wick Method," Klin. Wochenschr.67:491–495 (1989); and Pickup, et al.,: "In Vivo Molecular Sensing in Diabetes Mellitus: An Implantable Glucose Sensor with Direct Electron Transfer," Diabetologia 32:213–217 (1989). Other sensors are described in, for example Reach, et al., in ADVANCES IN IMPLANTABLE DEVICES, A. Turner (ed.), JAI Press, London, Chap. 1, (1993), incorporated herein by reference.

While intravascular stents and glucose sensors are discussed as preferred devices for use with the polymer coatings disclosed herein, artisans understand that the polymer compositions can be utilized with a wide variety of devices known in the art such as medication delivery pumps, catheters, balloons, wire guides, cannulae, and the like.

Various citations are referenced throughout the specification (e.g. U.S. Pat. No. 6,322,815). In addition, certain text from related art is reproduced herein to more clearly delineate the various embodiments of the invention. The disclosures of all citations in the specification are expressly incorporated herein by reference.

What is claimed is:

1. An implantable medical device having at least one polymer coating composition, the polymer coating prepared from a reaction mixture of:
   (a) a diisocyanate, the diisocyanate comprising about 50 mol % of the reactants in the mixture;
   (b) a hydrophilic polymer which is a member selected from the group consisting of a hydrophilic polymer diol, a hydrophilic polymer diamine and combinations thereof;
   (c) a bioactive agent, wherein the bioactive agent is an anti-thrombocytic, anti-inflammatory or anti-proliferative agent; and optionally;
   (d) a chain extender.

2. The medical device of claim 1, wherein the reaction mixture further comprises a siloxane polymer having functional groups at the chain termini.

3. The medical device of claim 2, wherein the functional groups are members selected from the group consisting of amino, hydroxyl and carboxylic acid.

4. The medical device of claim 1, wherein the bioactive agent is capable of being released from the polymer coating into the environment in which the medical device is placed.

5. The medical device of claim 4, wherein the release of the bioactive agent from the polymer coating is modulated by the diffusion coefficient of the polymer coating.

6. The medical device of claim 4, wherein the device has a plurality of polymer coatings having a plurality of diffusion coefficients, and wherein the release of the bioactive agent from the polymer coating is modulated by the plurality of polymer coatings.

7. The medical device of claim 4, wherein the release of the bioactive agent from the polymer coating is modulated by the pH of the polymer coating composition.

8. The medical device of claim 4 wherein the release of the bioactive agent from the polymer coating is modulated by hydrogen peroxide.

9. The medical device of claim 1, wherein the bioactive agent is rapamycin, heparin or an antisense oligonucleotide.

10. The medical device of claim 1, wherein the device is an intravascular stent.

11. The medical device of claim 1, wherein the reaction mixture further comprises glucose oxidase.

12. The medical device of claim 11, wherein the polymer coating has a glucose diffusion coefficient of from about $1 \times 10^{-9}$ cm$^2$/sec to about $200 \times 10^{-9}$ cm$^2$/sec, and a ratio of $D_{oxygen}/D_{glucose}$ of from about 5 to about 2000.

13. The medical device of claim 1, wherein the polymer coating has a water pickup of from about 25% to about 400% by weight.

14. The medical device of claim 1, wherein the diisocyanate,is a member selected from the group consisting of isophorone diisocyanate, 1,6-hexamethylene diisocyanate and 4,4'-methylenebis(cyclohexyl isocyanate).

15. The medical device of claim 1, wherein the reaction mixture further comprises a chain extender.

16. The medical device of claim 1, wherein the chain extender is selected from the group consisting of an alkylene dial, an alkylene diamine, an aminoalkanol and combinations thereof.

17. The medical device of claim 1, wherein the diisocyanate is 1,6-hexamethylene diisocyanate, the hydrophilic polymer is selected from the group consisting of PEG 400 and PEG 600 and is present in an amount of about 17 to about 32 mol%, and the siloxane polymer is aminopropyl polysiloxane having a molecular weight of about 2000 to about 4000 and is present in an amount of about 17 to about 32 mol %.

18. An implantable medical device having at least one polymer coating composition, the polymer coating prepared from a reaction mixture of:
 (a) a diisocyanate, the diisocyanate comprising about 50 mol % of the reactants in the mixture;
 (b) a hydrophilic polymer which is a member selected from the group consisting of a hydrophilic polymer diol, a hydrophilic polymer diamine and combinations thereof;
 (d) glucose oxidase;
 (c) a bioactive agent wherein the bioactive agent is capable of being released from the polymer coating into the environment in which the medical device is placed, and wherein the bioactive agent is an anti-thrombocytic, anti-inflammatory or anti-proliferative agent;
 wherein the release of the bioactive agent is modulated by a product that is produced from a reaction between the glucose oxidase that is present in the polymer coating and glucose that is present environment in which the medical device is placed.

* * * * *